(12) United States Patent
Liu

(10) Patent No.: US 9,526,919 B2
(45) Date of Patent: Dec. 27, 2016

(54) MULTI-PURPOSE RADIATION THERAPY SYSTEM

(71) Applicant: Cybermed Technologies (Xi'an) Co., Ltd., Xi'an, Shanxi Province (CN)

(72) Inventor: Haifeng Liu, Xi'an (CN)

(73) Assignee: CYBERMED TECHNOLOGIES (XI'AN) CO., LTD., Xi'An (CN)

( * ) Notice: Subject to any disclaimer, the term of this patent is extended or adjusted under 35 U.S.C. 154(b) by 55 days.

(21) Appl. No.: 14/437,333

(22) PCT Filed: Nov. 1, 2013

(86) PCT No.: PCT/CN2013/086462
§ 371 (c)(1),
(2) Date: Apr. 21, 2015

(87) PCT Pub. No.: WO2015/062093
PCT Pub. Date: May 7, 2015

(65) Prior Publication Data
US 2016/0038768 A1 Feb. 11, 2016

(51) Int. Cl.
*A61N 5/10* (2006.01)
*G21K 1/04* (2006.01)

(52) U.S. Cl.
CPC ........... *A61N 5/1081* (2013.01); *A61N 5/1039* (2013.01); *A61N 5/1047* (2013.01); *A61N 5/1082* (2013.01); *A61N 5/1084* (2013.01)

(58) Field of Classification Search
CPC ...... A61N 5/1084; A61N 5/1081; A61N 5/01; A61N 5/10; A61N 5/1065; A61N 5/1077; A61N 5/1082; G21K 1/046

USPC ........ 378/65, 207, 63, 64; 250/341.7, 494.1, 250/505.1; 600/427
See application file for complete search history.

(56) References Cited

U.S. PATENT DOCUMENTS

| 5,537,452 A * | 7/1996 | Shepherd ............... A61N 5/103 378/148 |
| 7,831,013 B2 * | 11/2010 | Star-Lack .............. A61B 6/025 378/23 |
| 7,835,492 B1 | 11/2010 | Sahadevan |
| 7,902,530 B1 | 3/2011 | Sahadevan |
| 8,139,714 B1 * | 3/2012 | Sahadevan ............. A61N 5/025 378/63 |
| 8,173,983 B1 * | 5/2012 | Sahadevan ........... A61N 5/1084 250/341.7 |

(Continued)

FOREIGN PATENT DOCUMENTS

| CN | 1355055 A | 6/2002 |
| CN | 102939607 A | 2/2013 |

*Primary Examiner* — David A Vanore

(57) ABSTRACT

The present invention relates to a multi-purpose radiation therapy system. The radiation therapy system comprises a base, a movable couch, a rotatable gantry, and a radiotherapeutic apparatus. The movable couch and the rotatable gantry are arranged on the base, while the movable couch is sleeved in the rotatable gantry, and the radiotherapeutic apparatus is movably installed on the rotatable gantry. The radiotherapeutic apparatus includes a multi-source focusing radiotherapeutic unit and an adaptive intensity modulated radiotherapeutic unit. The multi-source focusing radiotherapeutic unit and the adaptive intensity modulated radiotherapeutic unit are distributed at both sides of a rotatable gantry axis, and are connected to the rotatable gantry via respective arc guide rail.

11 Claims, 2 Drawing Sheets

(56) References Cited

U.S. PATENT DOCUMENTS

| | | | | |
|---|---|---|---|---|
| 8,254,521 | B2* | 8/2012 | Brooks | A61B 6/502 |
| | | | | 378/37 |
| 8,300,766 | B2* | 10/2012 | Handa | A61B 6/022 |
| | | | | 378/207 |
| 8,637,841 | B2* | 1/2014 | Prince | G21K 1/046 |
| | | | | 250/492.1 |
| 8,682,414 | B2* | 3/2014 | Nishimoto | A61N 5/103 |
| | | | | 378/62 |
| 8,712,011 | B2* | 4/2014 | Robar | A61N 5/1049 |
| | | | | 378/62 |
| 9,149,654 | B2* | 10/2015 | Handa | A61N 5/1049 |
| 9,149,656 | B2* | 10/2015 | Tanabe | A61N 5/1067 |
| 9,155,910 | B1* | 10/2015 | Sahadevan | A61N 5/1077 |
| 9,283,403 | B2* | 3/2016 | Mazin | A61B 6/037 |
| 2012/0307973 | A1* | 12/2012 | Dirauf | A61B 6/032 |
| | | | | 378/62 |
| 2014/0321615 | A1* | 10/2014 | Carlsson | A61N 5/1049 |
| | | | | 378/62 |
| 2015/0251022 | A1* | 9/2015 | Liu | A61N 5/1081 |
| | | | | 600/1 |
| 2016/0220848 | A1* | 8/2016 | Adler, Jr. | A61N 5/1081 |
| | | | | 378/65 |

* cited by examiner

MULTI-PURPOSE RADIATION THERAPY SYSTEM

TECHNICAL FIELD

The present invention relates to the technical field of large medical device, and in particular, to a multi-purpose radiation therapy system.

BACKGROUND

Medical equipment for radiation therapy treats tumorous tissue with high energy radiation. Two types of radiation therapy methods are generally employed for radiation therapy, namely, stereotaxic multi-source focusing radiation therapy method and adaptive intensity modulated radiation therapy (IMRT) method. Regarding the stereotaxic multi-source focusing radiation therapy method, a plurality of radioactive rays are focused to one focal point (namely, the target region), so that high-dose irradiation is performed on the tumor which is in the target region. This multi-source focusing radiation therapy method may be adopted to perform high-dose irradiation for tumor tissues, while radiation damage for surrounding tissues is small. This multi-source focusing radiation therapy method, with a precise therapeutic property, has a very good therapeutic effect for intracranial tumors or head and neck tumors. However, for a body tumor that has a complicated shape or that is large, the foregoing multi-source focusing radiation therapy method has its limits, and the conformal knife radiation therapy method is required. The conformal knife radiation therapy method adopts a single radioactive source, which is conformally processed and enables a distribution shape of a radiation dose region to be identical with or the same as the shape of the tumor in three dimensions, thereby avoiding or decreasing irradiation for normal tissues. In addition, the radiation dose in the dose region is uniformly distributed.

Currently, there is no radiation therapy device that can integrate the stereotaxic multi-source focusing radiation therapy method with the adaptive intensity modulated radiation therapy method. In other words, the current radiation therapy devices cannot implement both accurate multi-source focusing therapy and conformal therapy on one device. For patients, different therapy methods cannot be selected for different tumors or a same tumor on a same device.

SUMMARY

The present invention provides a medical device that integrates stereotaxic multi-source focusing radiation therapy with conformal radiation therapy, which can implement both accurate focusing therapy and adaptive intensity modulated therapy on one radiation therapy device.

An embodiment of the present invention provides A multi-purpose radiation therapy system, comprising a base, a movable couch, a rotatable gantry, and a radiotherapeutic apparatus, the movable couch and the rotatable gantry being arranged on the base, and the radiotherapeutic apparatus being movably installed on the rotatable gantry, wherein the radiotherapeutic apparatus comprises a multi-source focusing radiotherapeutic unit and an adaptive intensity modulated radiotherapeutic unit and the multi-source focusing radiotherapeutic unit and the adaptive intensity modulated radiotherapeutic unit are distributed at both sides of a rotatable gantry axis, and are connected via respective arc guide rail.

Preferably, an angle from the multi-source focusing radiotherapeutic unit to the adaptive intensity modulated radiotherapeutic unit relative to the axis center of the rotatable gantry is continuously adjustable between 30 degrees and 180 degrees.

Preferably, the multi-source focusing radiotherapeutic unit and the adaptive intensity modulated radiotherapeutic unit respectively swings around a focal point on a rotatable gantry axial plane, and a swinging angle is in a range of 0 to ±47.5 degrees.

Preferably, the rotatable gantry is 360-degree rotatable around the rotatable gantry axis in a continuous or reciprocal manner, to drive the multi-source focusing radiotherapeutic unit and the adaptive intensity modulated radiotherapeutic unit that are connected to the rotatable gantry to continuously or reciprocally rotate 360 degrees around the rotatable gantry axis. Preferably, an incident angle of the multi-source focusing radiotherapeutic unit and the adaptive intensity modulated radiotherapeutic unit exceeds $2\pi$.

Preferably, the multi-purpose radiation therapy system further comprises a dynamic image guide system, a set of stereo imaging apparatus or two sets of stereo imaging apparatuses at a fixed angle are installed on the rotatable gantry with the same focal point.

Preferably, an angle between two sets of imaging apparatuses in the stereo imaging apparatuses is in a range of 20 degrees to 160 degrees.

Preferably, the multi-source focusing radiotherapeutic unit comprises a plurality of radioactive sources, a precollimator, and a movable collimator, and rays of the radioactive sources pass through the precollimator and the movable collimator, and are focused on one point, to form a focused field.

Preferably, the movable collimator is provided with apertures in different size, and the movable collimator is configured to switch the apertures to change a size and a shape of the focused field.

Preferably, the adaptive intensity modulated radiotherapeutic unit comprises a radioactive source, a precollimator, and a multi-leaf collimator.

Preferably, the radioactive source of the adaptive intensity modulated radiotherapeutic unit is a single cobalt source or an X ray generator having an intensity greater than 4 mV.

By adopting the radiation therapy system of the embodiment of the present invention that integrates the stereotaxic multi-source focusing therapy with the adaptive intensity modulated therapy, the radiation therapy device can implement both the accurate focusing therapy and the adaptive intensity modulated radiation therapy.

DETAILED DESCRIPTION

To make the objective, technical solution, and advantages of the present invention more clear, the following section describes the technical solution of the present invention in combination with the accompanying drawings. It should be understood that the embodiment described here is only exemplary one for illustrating the present invention, and is not intended to limit the present invention.

Figure 1:
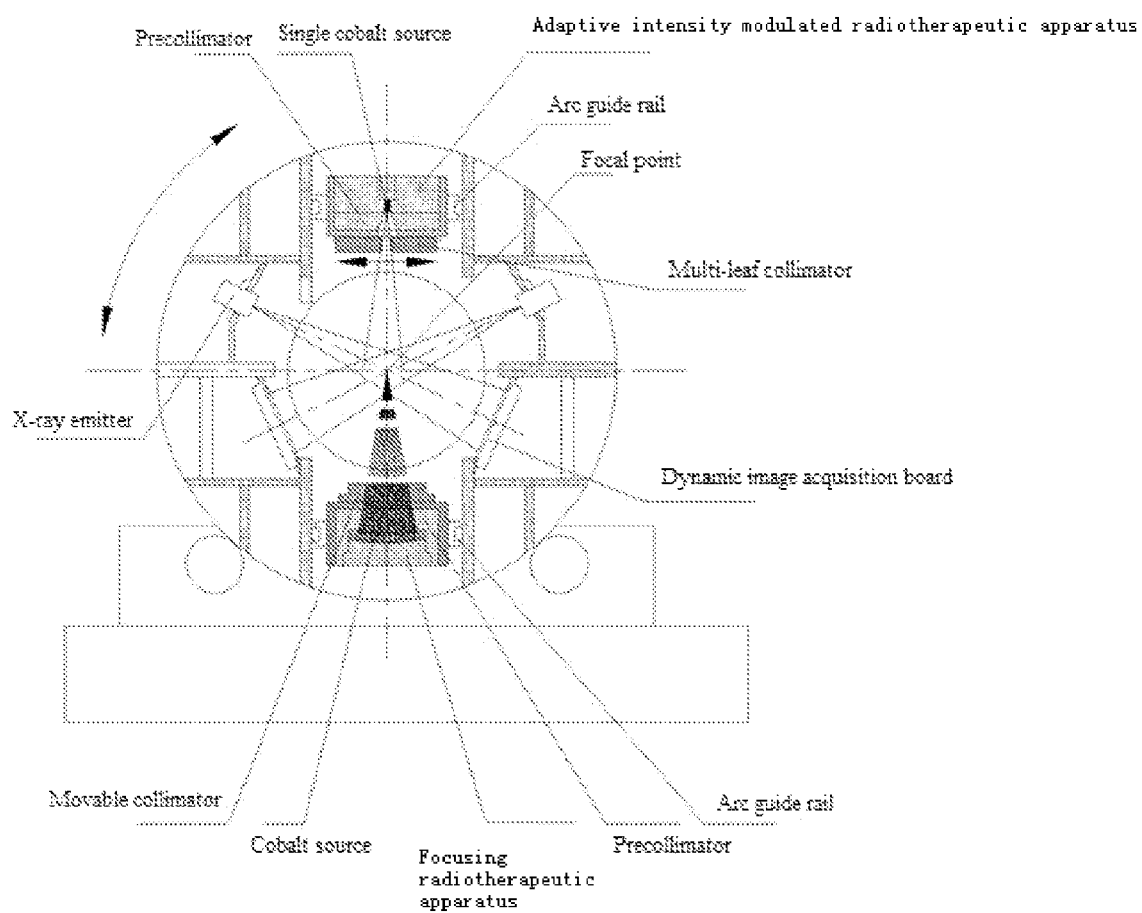
FIG. 1 is a schematic diagram of a multi-purpose radiation therapy system according to an embodiment of the present invention.
Figure 2:
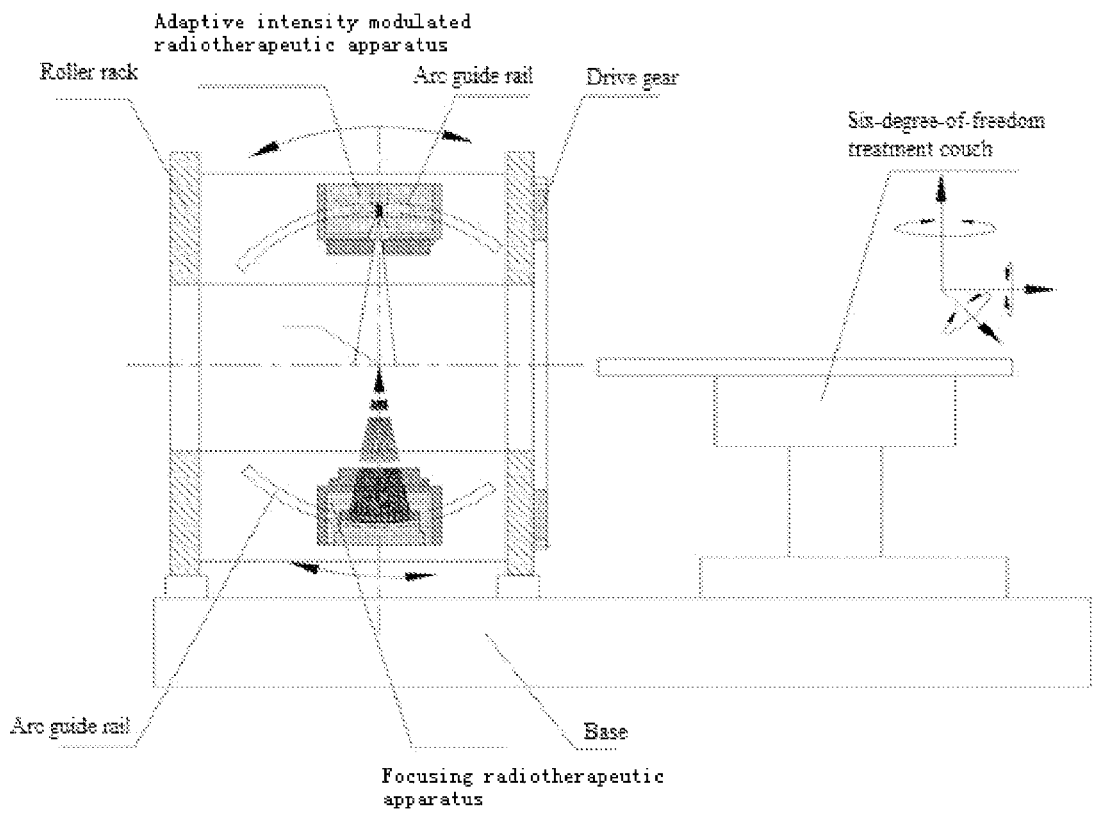
FIG. 2 is a side view of the multi-purpose radiation therapy system according to the embodiment of the present invention.

For a better understanding of the technical solution of the present invention, the applicant describes a multi-purpose radiation therapy system of the embodiment of the present invention by using detailed implementation manners of FIG. 1 and FIG. 2. FIG. 1 is a schematic diagram of a radiation therapy system that integrates stereotaxic multi-source focusing radiation therapy structure with adaptive intensity modulated radiation therapy structure according to an embodiment of the present invention. As shown in FIG. 1, the radiation therapy system comprises a base, a rotatable gantry, a radiotherapeutic apparatus, and a treatment couch. The base supports the whole radiation therapy system, and plays a role of bearing the whole radiation therapy system and a role of fixation. The treatment couch is arranged on the base, and is movably connected to the base, e.g. by using screws and pins. The treatment couch is used to support and position a patient, and can accurately deliver the patient to a specified position for treatment. The rotatable gantry is further arranged on the base, and is connected to the base by a rolling support. The rotatable gantry rotates around an axial line, which is defined as a rotatable gantry axis X, by means of, e.g. gear drive.

The radiation therapy system further comprises a core portion, namely, the radiotherapeutic apparatus. In one embodiment of the present invention, the radiotherapeutic apparatus involves two types of radiotherapeutic apparatuses, namely, a focusing radiotherapeutic apparatus and an adaptive intensity modulated radiotherapeutic apparatus. More specifically, the radiotherapeutic apparatus includes a focusing radiotherapeutic unit and an adaptive intensity modulated radiotherapeutic unit. The focusing radiotherapeutic unit may perform Stereotaxic Radiosurgery (SRS) or Imaging Guide Radiation Therapy (IGRT). The adaptive intensity modulated radiotherapeutic unit may perform 3-Dimensional Conformal Radiation Therapy (3D-CRT), or Intensity Modulated Radiation Therapy (IMRT), or Stereotactic Body Radiation Therapy (SBRT), or Imaging Guide Radiation Therapy (IGRT).

The focusing radiotherapeutic unit and the adaptive intensity modulated radiotherapeutic unit are distributed at both sides of the rotatable gantry axis X. Because the rotatable gantry rotates around the rotatable gantry axis X (i.e. the gyration center), the radiotherapeutic apparatuses are driven to continuously or reciprocally rotate 360 degrees around the rotatable gantry axis X. In addition, the focusing radiotherapeutic unit and the adaptive intensity modulated radiotherapeutic unit are connected to the rotatable gantry and movable along an axial direction of the rotatable gantry, via respective arc guide rail. In this way, the radiotherapeutic apparatuses may continuously swing around a focal point on a rotatable gantry axial plane, and a swinging angle is in a range of 0 to ±47.5 degrees, so as to implement non-coplanar focusing or conformal therapy with different incident angles, thereby carrying out tumor therapy more flexibly and effectively. Further, regarding the placement position of the focusing radiotherapeutic unit and the adaptive intensity modulated radiotherapeutic unit, an included angle from the focusing radiotherapeutic unit and the adaptive intensity modulated radiotherapeutic unit to the axis is continuously adjustable between 30 degrees and 180 degrees. Since the radiotherapeutic apparatuses can make a continuous incident angle change of maximum ±47.5 degrees and a central rotation of 360-degree winding, a treatment incident angle of the system may exceed 2π.

The focusing radiotherapeutic unit further comprises a plurality of radioactive sources, a movable collimator, and a precollimator. In the embodiment of the present invention, the radioactive sources adopt cobalt-60, and gamma rays generated by the cobalt-60 pass through the precollimator and the movable collimator, and are focused on one focal point. As such, a focused field, namely, a high-dose region for therapy, is formed. The movable collimator is provided with a plurality of apertures in different size, and the movable collimator is moved while aligning with the theradioactive sources. The movement of the movable collimator is performed to switch the apertures, so as to change a size and a shape of the focused field. As such, the focusing radiotherapeutic unit can be used to implement accurate therapy with a small field size and a high dose.

The adaptive intensity modulated radiotherapeutic unit comprises a radioactive source, a precollimator, and a multi-leaf collimator. In the embodiment of the present invention, the radioactive source may be a single cobalt source or an X ray generator having an intensity greater than 4 mV. The radioactive source cooperates with the a multi-leaf collimator to implement different field shapes on a treatment plane, so as to implement three-dimensional adaptive intensity modulated irradiation. The multi-leaf collimator is implement with generally used technology, and details will not be described in the embodiment of the present invention.

In addition, the radiation therapy system of the present invention further comprises a dynamic image guide system (IGS), In this embodiment, the dynamic image guide system (IGS) is stereo imaging apparatus, and one or two sets of stereo imaging apparatuses are assembled on the rotating rotatable gantry, and focus to the same focal point of the focusing radiotherapeutic unit and the adaptive intensity modulated radiotherapeutic unit. Generally, each set of the stereo imaging apparatus includes an X-ray generator and an image detection and acquisition system. Accordingly, one or two sets of X-ray imaging apparatuses are installed on the rotatable gantry, to perform real-time detection of a body position and a focus space position of a patient. Space position compensation is performed for the treatment couch and the radiotherapeutic apparatuses according to a detection result, so as to ensure high-precision orientation during treatment and implement accurate radiation therapy. When two sets of X-ray imaging apparatuses are adopted, an included angle of two sets of imaging apparatuses is in a range of 20 degrees to 160 degrees.

In the embodiment of the present invention, the multi-source focusing radiotherapeutic unit and the adaptive intensity modulated radiotherapeutic unit are integrated into one radiation therapy system, which has a great advantage for some special tumor focuses where two manners of multi-source focusing and intensity modulation are required simultaneously or separately for treatment. In the radiation therapy system, the adaptive intensity modulated radiotherapeutic unit and the multi-source focusing radiotherapeutic unit may be simultaneously or separately used for irradiation therapy with one positioning, to implement two types of combined radiation therapy, errors caused by multiple times of positioning are reduced, and radiation therapy precision and speed are improved, thereby improving quality and efficiency.

The above descriptions are merely a preferred embodiment of the present invention, but are not intended to limit the present invention. Any modification, equivalent replacement, or improvement made without departing from the spirit and principle of the present invention should fall within the protection scope of the present invention.

What is claimed is:

1. A multi-purpose radiation therapy system, comprising a base, a movable couch, a rotatable gantry, and a radiotherapeutic apparatus, the movable couch and the rotatable gantry being arranged on the base, and the radiotherapeutic apparatus being movably installed on the rotatable gantry, wherein, the radiotherapeutic apparatus comprises a multi-source focusing radiotherapeutic unit and an adaptive intensity modulated radiotherapeutic unit and the multi-source focusing radiotherapeutic unit and the adaptive intensity modulated radiotherapeutic unit are distributed at both sides of a rotatable gantry axis, and are connected via respective arc guide rail.

2. The multi-purpose radiation therapy system according to claim 1, wherein an angle from the multi-source focusing radiotherapeutic unit to the adaptive intensity modulated radiotherapeutic unit relative to the axis center of the rotatable gantry is continuously adjustable between 30 degrees and 180 degrees.

3. The multi-purpose radiation therapy system according to claim 1, wherein the multi-source focusing radiotherapeutic unit and the adaptive intensity modulated radiotherapeutic unit respectively swings around a focal point on a rotatable gantry axial plane, and a swinging angle is in a range of 0 to ±47.5 degrees.

4. The multi-purpose radiation therapy system according to claim 1, wherein the rotatable gantry is 360-degree rotatable around the rotatable gantry axis in a continuous or reciprocal manner, to drive the multi-source focusing radiotherapeutic unit and the adaptive intensity modulated radiotherapeutic unit that are connected to the rotatable gantry to continuously or reciprocally rotate 360 degrees around the rotatable gantry axis.

5. The multi-purpose radiation therapy system according to claim 4, wherein an incident angle of the multi-source focusing radiotherapeutic unit and the adaptive intensity modulated radiotherapeutic unit exceeds $2\pi$.

6. The multi-purpose radiation therapy system according to claim 1, further comprising a dynamic image guide system, a set of stereo imaging apparatus or two sets of stereo imaging apparatuses at a fixed angle are installed on the rotatable gantry with the same focal point.

7. The multi-purpose radiation therapy system according to claim 6, wherein an angle between two sets of imaging apparatuses in the stereo imaging apparatuses is in a range of 20 degrees to 160 degrees.

8. The multi-purpose radiation therapy system according to claim 1, wherein the multi-source focusing radiotherapeutic unit comprises a plurality of radioactive sources, a precollimator, and a movable collimator, and rays of the radioactive sources pass through the precollimator and the movable collimator, and are focused on one point, to form a focused field.

9. The multi-purpose radiation therapy system according claim 8, wherein the movable collimator is provided with apertures in different size, and the movable collimator is configured to switch the apertures to change a size and a shape of the focused field.

10. The multi-purpose radiation therapy system according to claim 1, wherein the adaptive intensity modulated radiotherapeutic unit comprises a radioactive source, a precollimator, and a multi-leaf collimator.

11. The multi-purpose radiation therapy system according to claim 10, wherein the radioactive source of the adaptive intensity modulated radiotherapeutic unit is a single cobalt source or an X ray generator having an intensity greater than 4 mV.

* * * * *